United States Patent [19]

Brambl

[11] Patent Number: 4,650,754

[45] Date of Patent: Mar. 17, 1987

[54] METHOD OF QUANTIFYING STORAGE MOLD CONTAMINATION

[75] Inventor: Robert M. Brambl, Minneapolis, Minn.

[73] Assignee: Regents of the University of Minnesota, Minneapolis, Minn.

[21] Appl. No.: 656,942

[22] Filed: Oct. 2, 1984

[51] Int. Cl.[4] .......................... C12Q 1/24; C12Q 1/06
[52] U.S. Cl. .......................................... 435/30; 435/31; 435/34; 435/39; 435/803; 435/913; 435/929
[58] Field of Search .................. 435/30, 31, 34, 39, 435/40, 803, 913, 929

[56] References Cited

U.S. PATENT DOCUMENTS

| | | | |
|---|---|---|---|
| 3,305,453 | 2/1967 | Singh et al. | 435/929 |
| 3,738,488 | 6/1973 | Hondermark | 435/803 |
| 3,950,224 | 4/1976 | Ward et al. | 435/803 |
| 4,086,141 | 4/1978 | Borowski et al. | 435/803 |

FOREIGN PATENT DOCUMENTS 0914567 12/1963 United Kingdom ................ 435/803

OTHER PUBLICATIONS

Industrial Microbiology, 4th ed., Prescot & Donn's, AVI Publishing Co., Inc., Westport, Conn., 1982, pp. 48-51.
Albert, Adrien, Selective Toxicity, 5th ed., 1973, Chapman and Hall, London, pp. 112-113.
Handbook of Microbiology (condensed ed.) 1974, CRC Press, USA, pp. 333-345 and 487.
Difco Manual (1977) 9th ed., Difco Laboratories Inc., Detroit, Michigan, pp. 73, 175-176 and 243-254.
Bonnen et al, (1983) Experimental Mycology, vol. 7, pp. 197-207.

*Primary Examiner*—Sam Rosen
*Assistant Examiner*—William J. Herald
*Attorney, Agent, or Firm*—Burd, Bartz & Gutenkauf

[57] ABSTRACT

A method for quantitatively determining the extent of mold contamination of grain and other mold-susceptible bulk food. The mold spores are selectively extracted from a small representative sample of the grain or other food by admixing with a solvent. After washing with a detergent, the extracted spores are suspended in a sterile solution and, in the case of heavy contamination, a series of graduated dilutions of known concentration are prepared. A measured sample of suspended spores is transferred to a nutrient growth medium and maintained under growth conditions until all possible spore colonies have developed. The spore colonies are counted. Since the dilution factor is known, the number of fungal spores in the original sample of stored product can readily be calculated.

18 Claims, No Drawings

METHOD OF QUANTIFYING STORAGE MOLD CONTAMINATION

BACKGROUND OF THE INVENTION

1. Field of the Invention

This invention is directed to a method for quantitatively determining the extent of mold contamination of grain and other food in storage. More particularly, the invention is directed to a method for quantifying storage mold contamination by selectively extracting mold spores from the stored commodity with a solvent, such as a paraffinic hydrocarbon or an aqueous detergent solution and determining the number of mold spores by quantitative microbiological procedures.

One of the most severe problems in the grain and food industry is the contamination and resulting deterioration of these stored commodities by fungi. Much research has been devoted to identifying conditions under which storage molds flourish, and the results of this research have pointed to ideal means of storing grain and other mold-susceptible bulk food to reduce losses. These preventative technologies, however, are expensive when generally applied to all stored commodities and their objectives are not always attained in practice. One of the major needs in applying existing preventative technologies is a reliable, sensitive means for assessing the extent of initial mold contamination of grain or food before transfer to storage and for monitoring development or increase in mold contamination during storage.

The most common and economically important group of grain storage molds is in the genus Aspergillus. The two common approaches for assessing contamination with this organism are (1) transfer of individual seeds to a mycological nutrient medium to observe the number of seeds from which fungi grow, and (2) pooling and grinding of a seed sample before transfer to mycological nutrient medium to observe the number of particles from which storage molds grow. The problem with the first approach is that only very small numbers of seeds can be processed feasibly. The second approach does not allow one to know whether one or a few seeds within the larger sample were heavily contaminated, or whether all the seeds were contaminated but to a lower extent. Importantly, neither method discriminates between light and heavy mold infestations. What is required instead is a means of assessing quantitatively the total load of storage molds in a relatively large sample of stored grain or other bulk stored food. Ideally, this procedure should be not only sensitive but sufficiently rapid and convenient to permit processing of replicate samples of the same lot of stored grain or food.

Members of the genus Fusarium may infest certain grains and under appropriate circumstances produce potent toxins that are hazardous to humans and livestock. No effective method is known for quantitatively determining Fusarium infestation.

2. The Prior Art

No prior art pertinent to the claimed method of quantifying storage mold contamination is known to applicant.

SUMMARY OF THE INVENTION

In carrying out the method for quantitatively determining the extent of mold contamination of grain and other mold-susceptible bulk food in storage, first a small representative sample of the stored product is selected. This sample product is thoroughly admixed with a solvent to selectively extract fungal spores present in the product. A preferred solvent for Asperoillus determinations is a paraffinic hydrocarbon. Aqueous detergent solutions are useful as solvents in the extraction of other types of spores, such as Fusarium, as well as Aspergillus. The extraction solvent containing the spores is removed from the product sample. Preferably the spore extraction is carried out in several stages and the several batches of extraction solvent are combined.

The extracted spores are then separated from the solvent, as by filtering. These separated spores are then preferably thoroughly washed to remove excess solvent. The washed extracted spores are transferred to and suspended in a sterile dilute detergent solution. The detergent is required to insure dispersal of spores that otherwise would aggregate. A measured sample of this suspension is transferred to a measured amount of sterile detergent solution to produce a suspension of known dilution. In the case of heavy infestation, a series of graduated further dilutions is prepared by transferring a measured sample from the first suspension to a further measured amount of sterile detergent solution, transferring a measured sample from the second dilution, and so on, through up to six or more successive dilutions.

A measured sample of suspended spores from the initial suspension or from each dilution is transferred to a solid mycological nutrient growth medium. Each is maintained under optimal fungal growth conditions for several days until all possible spore colonies have developed. The number of spore colonies developed in each dilution sample are counted. Since each colony derives from a single spore and since the dilution factor is known, the number of fungal spores present in the original stored product sample can readily be determined by calculation.

DETAILED DESCRIPTION OF THE PREFERRED EMBODIMENT

In its preferred form, the invention is a novel method of determining extent of Aspergillus contamination of grain and other mold-susceptible food which makes use of a paraffinic hydrocarbon to selectively extract the Aspergillus spores from the substrate and to determine their number by quantitative microbiological procedures. In the course of research into the molecular biology of spore germination (Bonnen and Brambl, Experimental Mycology, 7, 197–207, 1983), a procedure was developed to harvest the spores of *Neurospora crassa* (a fungus which does not contaminate stored grain) that prevented metabolic preactivation of the spores. It was found that a paraffinic hydrocarbon allowed the spores to selectively partition into this solvent while all traces of the parent mycelium and other substances were excluded.

The basis of this selective extraction is that the spores possess a coat protein which renders them extremely hydrophobic and difficult to wet with water. It seemed that these spores would be more soluble in a non-aqueous solvent as long as they possessed the hydrophobic spore coat. The procedure proved to be an extremely useful experimental tool, but it also seemed possible to extend the extraction technique to other types of fungi whose spores might also possess a hydrophobic coat. Aspergillus spores were then determined to be selectively solubilized from in vitro culture with the paraffinic hydrocarbon. Subsequently experiments were undertaken to determine if Aspergillus spores could be selectively extracted from samples of contaminated grain without simultaneously extracting other seed debris.

In practice a sample of grain or seeds is combined with the paraffinic hydrocarbon, the size of the sample being of any weight that may be conveniently manipulated. The grain and solvent are combined in a ratio of about 6 liquid units of solvent for each unit by weight (ml/g) of grain or other food. Thus a sample of grain is combined with the solvent in an approximate ratio of 10 gm of solid to 60 ml solvent. The solid material is mixed thoroughly with the solvent with a mechanical rotary shaker at 200 rpm for 5 minutes. The liquid is decanted, set aside, and the solids are re-extracted three times with 50 ml of the solvent in each successive extraction. Each of the three secondary extraction fluids is combined with the initial extraction fluid. Whole grains such as corn, and seeds such as soybean, are extracted directly without grinding or disintegration. Peanuts should first have their husks broken open for extraction of the kernels as well as the husks. Foodstuffs such as pet food may be extracted directly or coarsely ground before extraction. The combined extraction fluids are then poured through a fine micropore filter, such as a 0.8 micron Millipore filter (or equivalent) mounted in a filtration chimney for quantitative recovery. The extracted spores are retained on the filter surface, and the extraction solvent is passed through the filter and discarded.

The spores remaining on the filter are then washed extensively with a mild aqueous detergent solution to remove excess solvent. A sterile 1% solution in water of Nonidet P-40 (Shell Chemical Co.), a non-ionic detergent (octylphenoxypolyethoxyethanol) has been used, although other detergents such as the polyoxyethylene solutions (Tween 40, Tween 60, Tween 80) or Brij in water at concentrations from about 0.5% to 5% may be used with varying, but decreased, effectiveness. The spores should be washed at least with 75 ml of detergent solution for each 10 gm of solid originally extracted, and the volume of the wash fluid should be increased for heavily infested samples. The entire filter with spores adhering is then transferred to a sterile tube containing 10 ml of sterile detergent, such as 1% Nonidet P-40. The tube is agitated to wash spores from the filter into the fluid. One ml of this suspension is then transferred to 9 ml of sterile detergent solution, such as 1% Nonidet P-40 in water in another tube and mixed. The transfer of one ml of this suspension to another 9 ml tube follows. In this way a dilution series of the original spore suspension is made, and the original sample is diluted from 1:10 to 1:1,000,000. Where mold infestation is light, dilution of the original suspension may not be necessary.

Samples (0.15 ml) are removed from each of the dilution tubes and transferred to a mycological nutrient growth medium solidified with agar in Petri plates. The samples are spread uniformly over the agar surface with a turntable and a straightedged glass rod. The composition of the nutrient agar medium in part determines the types of molds that will be quantified subsequently. A selective medium containing high salt, such as Difco powdered tomato juice agar (25 gm), powdered agar (15 gm); NaCl (60 gm); and water (900 ml) may be used because it allows growth of common storage fungi, such as the Aspergilli, that tolerate high osmotic pressure while also inhibiting growth of most other organisms that might be present. Other types of selective nutrient media may be employed to selectively isolate and quantitate other types of microorganisms present in the grain or food sample.

Within about three days at ambient laboratory temperature and light, small, discrete colonies begin to appear on the agar surface, and within about five days all colonies have developed. The bottom surfaces of the Petri plates are marked with a felt-tip pen to score the colonies as they develop and to quantitate the number of colony-forming units or spores present in the dilution sample. If one knows the dilution factor, it then is possible to determine the number of spores present in the original seed or grain sample, as shown in the example below.

As an example, three equivalent subsamples are removed from the initial grain sample, and each subsample is extracted as described. Each of the subsample extracts may then be carried through the entire dilution series for subsequent plating, and two of the steps within this range should yield countable dilution plates (for a total of eighteen plates from the three subsamples, the three replicate platings, and a two-fold range of dilutions that yield reliable colony counts). The technician may average the results of the two adjacent dilution platings that are scored, or the plates bearing a much lower (and less reliable) number of spores may be discarded. The total number of colonies on a plate is multiplied by its dilution factor and by a constant factor of 66.67 (the proportion between the 10 ml dilution volume and the 0.15 ml removed for plating) to give the number of spores in the original 10 ml of detergent solution in which the extracted spores were resuspended from the filter. If 23 colonies were counted on an agar plate containing 0.15 ml of a $10^{-3}$ (or 1:1000) dilution, after multiplication by 66.67 one concludes that the grain subsample contained about 1,533,410 spores. Observing 19 and 26 colonies on the other replicate plates, followed by an averaging of the three values, yields an estimate of 1,511,000 spores per subsample. The averages of the three subsamples then yields an estimate for the grain sample.

The dilution series over a multi-decade range is necessary for quantitation of unknown samples, since some samples may be relatively heavily infested with molds whereas other samples may have low concentrations. In quantifying numbers of spores from a solid sample, one may discard the assay plates on either side of the countable range, since the number of colonies on those plates may be too numerous or too few to count accurately.

In practice, it is desirable to extract as many subsamples as possible to accurately determine extent of infestation of grain or seeds, since contaminated solids are not always homogeneous. Furthermore, it is advisable to plate out triple replicates of each dilution tube to minimize and account for assay error. Hemacytometer assays of the diluted spore suspensions may be used for a rapid (15 min.) estimate of the spore load of the extracted grain sample, but the plating assay is essential because it is not confounded by the presence of contaminating debris and other types of mold spores.

A preferred extraction solvent is a synthetic isoparaffinic hydrocarbon liquid sold as Soltrol 170 (Phillips Chemical Company, Borger, Tex.) consisting of $C_{13}$ and $C_{14}$ isomers (density 0.778 gm/cc; kinematic viscosity: 2.47). Other solvents which may be used include pentanes, hexanes, heptanes, cycloparaffins (neapthenes), and other isoparaffins, but the suitability of these substitutes may vary in the efficiency of extraction and in toxicity to the spores.

The described method for assessing contamination of stored grain and seeds with Aspergillus molds is useful for determination of initial extent of infestation before the commodity is transferred to storage, and is useful for monitoring possible changes in infestation during storage. The technique described has proved to be extremely sensitive and capable of detecting the presence of spores at extremely low concentrations. The method makes it possible for commodity processors and researchers to determine absolute levels of contamination that are acceptable or hazardous. This technique possesses a sensitivity probably greater than is required to detect minimal or insignificant levels of contamination.

The method of this invention is especially useful for the analysis of peanuts, since this plant may become infested in the field with Aspergilli that produce severely carcinogenic aflatoxins. The contaminated peanuts thus are extremely hazardous for human or livestock consumption. It is important to peanut processors that the degree of contamination with Aspergillus be carefully assessed. Presently, there is no simple quantification system available, and quality assessment depends upon visual inspection.

The properties of the hydrocarbon extraction medium and the selective growth medium heavily favor final observation and quantification of the Aspergilli storage molds. We have seldom isolated any fungus from grain or seeds with this technique which was not identified as an Aspergillus species. Other types of mold spores may be isolated by this extraction technique, including the asexual conidia of a number of species of Penicillium, Neurospora, Trichoderma, Rhizopus, and Cladosporium. Co-contaminating fungi such as Fusarium are not soluble in the hydrocarbon extraction solvent, although, as described in detail below, by use of an aqueous solution of a detergent and a selective growth medium, the Fusaria also can be selectively isolated and quantified.

The significant features of the described hydrocarbon extraction method as compared to water based extraction methods are: (1) no impairment of viability allows for subsequent growth and identification; (2) no interfering residues from substances treated; and (3) samples can be stored.

The use of the paraffinic hydrocarbon together with the described high-salt nutrient medium heavily favors detection of Aspergillus species which are the prominent organisms involved in grain deterioration. However, there may be other circumstances in which a technician may wish to assess the total microbiological contamination of a foodstuff sample or to determine its specific contamination with another type of microbe. For this type of application, the use of a detergent solution combined with a general or selective nutrient medium, would be the method of choice since this solvent effectively extracts all types of organisms from stored grain. The composition of the nutrient medium onto which the extracted microbes are subsequently plated then would determine the types of organisms that are detected. Thus, aqueous solutions of non-ionic detergents may be employed for the grain and food extractions, and are useful in the extraction of other types of spores that would not be efficiently solubilized by the paraffinic hydrocarbon which extracts only those spores with hydrophobic properties.

The non-ionic detergent octylphenoxypolyethoxyethanol (Nonidet P-40) is an efficient, but non-selective extraction medium useful for grain and foodstuff analysis when the total load of fungal spores and bacteria in a grain sample should be extracted for quantitation. For example, members of the genus Fusarium may infest certain grains and under appropriate circumstances produce potent toxins that are hazardous to humans and livestock. The Nonidet P-40 will extract Fusarium spores from grain, and subsequent plating of the extracted samples on a suitable selective medium containing antibacterial antibiotics and a fungicide will strongly favor growth of only the Fusarium spores for quantitative analysis. The selective medium preferred for this analysis of Fusarium contamination contains the following ingredients: Peptone (15 g), $KH_2PO_4$ (1 g), $MgSO_4 \cdot 7H_2O$ (0.5 g), streptomycin sulfate (0.3 g), aureomycin, (0.05 g), pentachloronitrobenzene (1 g), agar (20 g), and $H_2O$ to 1000 ml. The extraction procedure and plating techniques are exactly those described for the hydrocarbon extraction, except that the initial extraction medium is the detergent instead of the paraffinic hydrocarbon and that the subsequent washing of the spores on the filter is unnecessary. The composition of the nutrient medium in the agar plates may also vary (as described), depending upon the type or range of organisms one wishes to assay.

The use of a high-salt tomato juice agar medium favors growth of Aspergillus and thus may be used for determination of Aspergillus contamination in grain from which the mold spores are extracted, along with other material, with a detergent solution. For isolation of Aspergillus species, the most important feature of the nutrient medium is the inclusion of a high concentration of an osmoticum such as salt (NaCl).

The invention is further illustrated by the following examples. The extraction and analysis procedures that have been determined experimentally for mold-infested corn, soybeans, and peanuts are identical. Experimental conditions that vary among the three extractions are related to the quantity of solid available for assay, the degree of mold infestation, and the dilution range at which reliable numbers of colonies are counted.

EXAMPLE I

Three ten-gram subsamples are removed from a sample of corn (originally obtained from a commercial grain elevator), and each is extracted in 60 ml of paraffinic hydrocarbon solvent, followed by three successive secondary extractions of the solid with 50 ml of the solvent. The combined extraction fluids are filtered as described, and the spores on the filter surface are washed with the detergent solution as described. A dilution series of the resuspended spores is established and aliquots of the diluted spore suspensions are plated onto the selective nutrient medium. The following data are used to calculate the number of spores present in the original solid sample:

| Subsample | Dilution | # Colonies in Replicate | Spores in Subsample (Dilution Factor × 66.67) | Subsample Average |
|---|---|---|---|---|
| 1 | $10^{-3}$ | 79 | 52,669,300 | |
| | | 92 | 61,336,400 | |
| | | 88 | 58,669,600 | |
| | $10^{-4}$ | 8 | 53,336,000 | |
| | | 8 | 53,336,000 | |
| | | 9 | 60,030,000 | 56,568,361 |

-continued

| Sub-sample | Di-lution | # Colonies in Replicate | Spores in Subsample (Dilution Factor × 66.67) | Subsample Average |
|---|---|---|---|---|
| 2 | $10^{-3}$ | 150 | 100,005,000 | |
| | | 160 | 106,672,000 | |
| | | 164 | 109,338,000 | |
| | $10^{-4}$ | 14 | 93,338,000 | |
| | | 14 | 93,338,000 | |
| | | 17 | 113,339,000 | 102,671,000 |
| 3 | $10^{-3}$ | 110 | 73,337,000 | |
| | | 99 | 66,003,300 | |
| | | 92 | 61,336,400 | |
| | $10^{-4}$ | 8 | 53,336,000 | |
| | | 9 | 60,003,000 | |
| | | 9 | 60,003,000 | 62,336,461 |

Thus, an average of the three subsamples indicates that 10 gm of this corn would be expected to contain about 73,855,441 mold spores. This average should account for variation between subsamples and experimental variation within an analysis.

EXAMPLE II

Three five-gram subsamples are removed from a sample of soybeans (originally obtained from a commercial grain elevator), and each is extracted in 60 ml of paraffinic hydrocarbon solvent, followed by three successive secondary extractions of the solid with 50 ml of the solvent. The combined extraction fluids are filtered as described, and the spores on the filter surface are washed with the detergent solution as described. A dilution series of the resuspended spores is established and aliquots of the diluted spore suspensions are plated onto the selective nutrient medium. The following data are used to calculate the number of spores present in the original solid sample:

| Sub-sample | Di-lution | # Colonies in Replicate | Spores in Subsample (Dilution Factor × 66.67) | Subsample Average |
|---|---|---|---|---|
| 1 | $10^{-1}$ | 42 | 280,014 | |
| | | 36 | 240,012 | |
| | | 43 | 286,681 | |
| | $10^{-2}$ | 3 | 200,010 | |
| | | 4 | 266,680 | |
| | | 4 | 266,860 | 256,680 |
| 2 | $10^{-1}$ | 36 | 240,012 | |
| | | 39 | 260,013 | |
| | | 32 | 213,344 | |
| | $10^{-2}$ | 3 | 200,010 | |
| | | 3 | 200,010 | |
| | | 3 | 200,010 | 218,899 |
| 3 | $10^{-1}$ | 29 | 193,343 | |
| | | 32 | 213,344 | |
| | | 40 | 266,680 | |
| | $10^{-2}$ | 2 | 133,340 | |
| | | 3 | 200,010 | |
| | | 3 | 200,010 | 211,122 |

Thus, an average of the three subsamples indicates that 5 gm of these soybeans would be expected to contain about 225,561 mold spores. This average should account for variation between subsamples and experimental variation within an analysis.

EXAMPLE III

Three ten-gram subsamples are removed from a sample of peanuts (originally obtained from the USDA National Peanut Research Laboratory), and after breaking open the hulls, each is extracted in 60 ml of paraffinic hydrocarbon solvent, followed by three successive secondary extractions of the solid with 50 ml of the solvent. The combined extraction fluids are filtered as described, and the spores on the filter surface are washed with the detergent solution as described. A dilution series of the resuspended spores is established and aliquots of the diluted spore suspensions are plated onto the selective nutrient medium. The following data are used to calculate the number of spores present in the original solid sample:

| Sub-sample | Di-lution | # Colonies in Replicate | Spores in Subsample (Dilution Factor × 66.67) | Subsample Average |
|---|---|---|---|---|
| 1 | $10^{-1}$ | 299 | 1,993,433 | |
| | | 276 | 1,840,092 | |
| | | 315 | 2,100,105 | |
| | $10^{-2}$ | 31 | 2,066,770 | |
| | | 29 | 1,933,430 | |
| | | 32 | 2,133,440 | 2,011,212 |
| 2 | $10^{-1}$ | 167 | 1,113,389 | |
| | | 180 | 1,200,060 | |
| | | 160 | 1,066,720 | |
| | $10^{-2}$ | 15 | 1,000,050 | |
| | | 17 | 1,133,390 | |
| | | 16 | 1,066,720 | 1,096,722 |
| 3 | $10^{-1}$ | 250 | 1,666,750 | |
| | | 266 | 1,773,422 | |
| | | 259 | 1,726,753 | |
| | $10^{-2}$ | 24 | 1,600,080 | |
| | | 26 | 1,733,420 | |
| | | 26 | 1,733,420 | 1,705,641 |

Thus, an average of the three subsamples indicates that 10 gm of these peanuts would be expected to contain about 1,604,524 mold spores. This average should account for variation between subsamples and experimental variation within an analysis.

EXAMPLE IV

Nonidet P-40 was used to extract mold-infested corn for determination of Aspergillus contamination through use of the high-salt tomato juice agar medium described elsewhere in this application. All procedures were identical to the previous examples of extractions except that the initial extraction medium was the detergent solution instead of the paraffinic hydrocarbon.

Three ten-gram subsamples are removed from a sample of corn (originally obtained from experimentally infested grain), and each is extracted in 60 ml of Nonidet P-40 (1% vol/vol in water), followed by three successive secondary extractions of the solid with 50 ml of the detergent. The combined extraction fluids are filtered as described, and the spores on the filter surface are washed with the detergent splution as described. A dilution series of the resuspended spores is established and aliquots of the diluted spore suspensions are plated onto the selective nutrient medium. The following data are used to calculate the number of spores present in the original solid sample:

| Sub-sample | Di-lution | # Colonies in Replicate | Spores in Subsample (Dilution Factor × 66.67) | Subsample Average |
|---|---|---|---|---|
| 1 | $10^{-3}$ | 50 | 33,335,000 | |
| | | 45 | 30,001,500 | |
| | | 44 | 29,334,800 | |
| | $10^{-4}$ | 4 | 26,668,000 | |
| | | 4 | 26,668,000 | |
| | | 5 | 33,335,000 | 29,890,383 |
| 2 | $10^{-3}$ | 41 | 27,334,700 | |
| | | 40 | 26,668,000 | |

| Sub-sample | Di-lution | # Colonies in Replicate | Spores in Subsample (Dilution Factor × 66.67) | Subsample Average |
|---|---|---|---|---|
|  |  | 43 | 28,668,100 |  |
|  | $10^{-4}$ | 4 | 26,668,000 |  |
|  |  | 4 | 26,668,000 |  |
|  |  | 4 | 26,668,000 | 27,112,467 |
| 3 | $10^{-3}$ | 46 | 30,668,200 |  |
|  |  | 42 | 28,001,400 |  |
|  |  | 39 | 26,001,300 |  |
|  | $10^{-4}$ | 5 | 33,335,000 |  |
|  |  | 4 | 26,668,000 |  |
|  |  | 3 | 20,001,000 | 27,445,817 |

Thus, an average of the three subsamples indicates that 10 gm of this corn would be expected to contain about 28,149,555 mold spores. This average should account for variation between subsamples and experimental variation within an analysis.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method for quantitatively determining the extent of mold contamination of grain and other mold-susceptible bulk food in storage which comprises:
   (A) selecting a small representative sample of the stored product,
   (B) thoroughly admixing the sample product with a solvent to extract fungal spores present in the product,
   (C) removing the extraction solvent and spores from the product sample,
   (D) separating the extracted spores from the solvent,
   (E) suspending the extracted spores in a sterile detergent solution,
   (F) transferring a sample from the suspension to a solid mycological nutrient medium and subjecting, the medium to growth conditions for several days until all possible spore colonies have developed, and
   (G) counting the number of spore colonies in the sample and from the known dilution factor determining the number of spores present in the original stored product sample.

2. The method of claim 1 wherein the extracted spores separated from the solvent are thoroughly washed with a dilute detergent solution to remove excess solvent.

3. The method of claim 2 wherein the extracted spores are washed with at least 7.5 liquid units of detergent solution for each unit by weight (ml/g) of original stored product sample.

4. The method of claim 3 wherein said detergent is a 0.5% to 5% solution of a non-ionic detergent in water.

5. The method of claim 4 wherein said detergent is octylphenoxypolyethoxyethanol.

6. The method of claim 1 wherein the extracted spores are separated from the solvent by micropore filtration.

7. The method of claim 1 wherein:
   (A) a series is prepared of graduated known dilutions of the initial suspension of the extracted spores in a sterile detergent solution,
   (B) a uniform sample from each dilution is transferred to a solid mycological nutrient medium and subjected to growth conditions for several days until all possible spore colonies have developed,
   (C) the number of spore colonies in each dilution sample are counted and from the known dilution factor the number of spores present in the original stored product sample are determined.

8. The method of claim 7 wherein the extracted spores are suspended in a series of graduate, dilutions, the number of dilutions being determined by the estimated degree of contamination of the stored food, each successive dilution having the same fractional concentration of spores, of the preceding sample.

9. The method of claim 8 wherein the extracted spores are suspended in a series of at least six graduated dilutions, each successive dilution having one tenth the concentration of spores of the preceding sample.

10. The method of claim 1 wherein the spore cultures are maintained under growth conditions for at least 5 days.

11. The method of claim 7 wherein the number of spores in the original sample is determined by:
   (A) counting the number of colonies on a plate,
   (B) multiplying the number by the dilution factor and by a constant factor representing the proportion between the dilution volume and sample volume removed for plating, and
   (C) averaging the results of several samples.

12. The method of claim 1 wherein:
   (A) the mold contamination is of the genus Aspergillus,
   (B) the solvent is a synthetic isoparaffinic hydrocarbon liquid, and
   (C) the medium is a high salt medium.

13. The method of claim 12 wherein the medium is a powdered tomato juice agar medium.

14. The method of claim 1 wherein:
   (A) the mold contamination is of the genus Aspergillus,
   (B) the solvent is an aqueous non-ionic detergent solution, and
   (C) the medium is a high salt medium.

15. The method of claim 14 wherein the detergent is octylphenoxypolyethoxyethanol.

16. The method of claim 14 wherein the medium is a powdered tomato juice agar medium.

17. The method of claim 1 wherein:
   (A) the mold contamination is of the genus Fusarium,
   (B) the solvent is an aqueous non-ionic detergent solution, and
   (C) the medium is a high peptone nutrient agar medium containing antibacterial antibiotics and a fungicide effective against Fusarium.

18. The method of claim 17 wherein the detergent is octylphenoxypolyethoxyethanol.

* * * * *